US009442011B2

(12) United States Patent
Morris et al.

(10) Patent No.: US 9,442,011 B2
(45) Date of Patent: Sep. 13, 2016

(54) METHODS FOR CALIBRATING A MULTIPLE DETECTOR SYSTEM

(71) Applicants: Jonathan M. Morris, Baton Rouge, LA (US); Yousheng Zeng, Baton Rouge, LA (US)

(72) Inventors: Jonathan M. Morris, Baton Rouge, LA (US); Yousheng Zeng, Baton Rouge, LA (US)

(73) Assignee: ExxonMobil Upstream Research Company, Spring, TX (US)

( * ) Notice: Subject to any disclaimer, the term of this patent is extended or adjusted under 35 U.S.C. 154(b) by 0 days.

(21) Appl. No.: 14/727,532

(22) Filed: Jun. 1, 2015

(65) Prior Publication Data
US 2015/0373285 A1 Dec. 24, 2015

Related U.S. Application Data

(60) Provisional application No. 62/015,926, filed on Jun. 23, 2014.

(51) Int. Cl.
*G01N 21/00* (2006.01)
*G01J 3/28* (2006.01)
*G01N 21/27* (2006.01)
(Continued)

(52) U.S. Cl.
CPC ............... *G01J 3/28* (2013.01); *G01J 3/2803* (2013.01); *G01J 3/36* (2013.01); *G01J 3/42* (2013.01); *G01N 21/274* (2013.01);
(Continued)

(58) Field of Classification Search
CPC ........................................................ G01N 21/00
See application file for complete search history.

(56) References Cited

U.S. PATENT DOCUMENTS 3,805,074 A 4/1974 McCormack
5,024,530 A 6/1991 Mende
(Continued)

FOREIGN PATENT DOCUMENTS

DE 43 24 154 7/1993
EP 2 549 744 1/2013
(Continued)

OTHER PUBLICATIONS

U.S. Appl. No. 62/015,920, filed Jun. 23, 2014, Morris et al.
(Continued)

*Primary Examiner* — David Porta
*Assistant Examiner* — Hugh H Maupin
(74) *Attorney, Agent, or Firm* — ExxonMobil Upstream Research Company—Law Department

(57) ABSTRACT

Methods for calibrating multiple electromagnetic radiation detectors within a detection system and methods of using such calibrated systems which include generating a calibration electromagnetic radiation beam at a first temperature. At least a portion of the calibration electromagnetic radiation beam is detected with a first electromagnetic radiation detector. An average intensity value of a plurality of pixels from the first electromagnetic radiation detector is obtained. One or more pixels of the first electromagnetic radiation detector are adjusted to decrease the difference between the intensity of an individual pixel and the average intensity value of the first electromagnetic radiation detector. Detecting at least a portion of the calibration electromagnetic radiation beam with a second electromagnetic radiation detector. One or more pixels of the second electromagnetic radiation detector are adjusted to decrease the difference between the intensity of an individual pixel and the average intensity value of the first electromagnetic radiation detector.

16 Claims, 2 Drawing Sheets

(51) Int. Cl.
| | |
|---|---|
| *G01N 21/31* | (2006.01) |
| *G01J 3/36* | (2006.01) |
| *G01J 3/42* | (2006.01) |
| *G01N 21/3504* | (2014.01) |

(52) U.S. Cl.
CPC ....... *G01N 21/314* (2013.01); *G01N 21/3504* (2013.01); *G01N 2021/3531* (2013.01)

(56) References Cited

U.S. PATENT DOCUMENTS

| | | |
|---|---|---|
| 5,210,702 A | 5/1993 | Bishop et al. |
| 5,252,060 A | 10/1993 | McKinnon et al. |
| 5,306,913 A | 4/1994 | Noack et al. |
| 5,430,293 A | 7/1995 | Sato et al. |
| 5,445,795 A | 8/1995 | Lancaster et al. |
| 5,446,445 A | 8/1995 | Bloomfield et al. |
| 5,656,813 A | 8/1997 | Moore et al. |
| 5,908,600 A | 6/1999 | Simi et al. |
| 5,932,818 A | 8/1999 | Novick et al. |
| 5,999,652 A | 12/1999 | Bushman |
| 6,061,141 A | 5/2000 | Goldenberg et al. |
| 6,476,859 B1 | 11/2002 | Galloway et al. |
| 6,618,712 B1 | 9/2003 | Parker et al. |
| 6,690,472 B2 | 2/2004 | Kulp et al. |
| 6,791,088 B1 | 9/2004 | Williams, II et al. |
| 6,803,577 B2 | 10/2004 | Edner et al. |
| 6,822,742 B1 | 11/2004 | Kalayeh et al. |
| 6,853,452 B1 * | 2/2005 | Laufer .......................... 356/436 |
| 6,866,089 B2 | 3/2005 | Avila |
| 6,943,353 B2 | 9/2005 | Elmore et al. |
| 6,995,360 B2 | 2/2006 | Jones et al. |
| 6,995,846 B2 | 2/2006 | Kalayeh et al. |
| 7,039,221 B1 | 5/2006 | Tumey et al. |
| 7,164,132 B2 | 1/2007 | Didomenico et al. |
| 7,189,970 B2 | 3/2007 | Racca et al. |
| 7,315,377 B2 | 1/2008 | Holland et al. |
| 7,358,860 B2 | 4/2008 | Germouni et al. |
| 7,375,814 B2 | 5/2008 | Reichardt et al. |
| 7,486,399 B1 | 2/2009 | Reichardt et al. |
| RE40,767 E | 6/2009 | Peterson et al. |
| 7,649,174 B2 | 1/2010 | Mammen et al. |
| 7,687,776 B2 | 3/2010 | Baliga et al. |
| 7,840,380 B2 | 11/2010 | Bernhardt |
| 7,939,804 B2 | 5/2011 | Schmidt |
| 7,977,639 B2 | 7/2011 | Maillart et al. |
| 8,009,932 B2 | 8/2011 | Zhou et al. |
| 8,085,301 B2 | 12/2011 | Hill, Jr. et al. |
| 8,117,010 B2 | 2/2012 | Busch et al. |
| 8,124,931 B2 | 2/2012 | Andrews et al. |
| 8,134,127 B2 | 3/2012 | Hill, Jr. |
| 8,134,711 B2 | 3/2012 | Hager |
| 8,193,496 B2 | 6/2012 | Furry |
| 8,212,210 B2 | 7/2012 | Hargel |
| 8,432,451 B2 | 4/2013 | Cetin et al. |
| 2004/0005715 A1 | 1/2004 | Schabron et al. |
| 2004/0015336 A1 | 1/2004 | Kulesz et al. |
| 2004/0027494 A1 | 2/2004 | Thomas |
| 2004/0211900 A1 | 10/2004 | Johnson |
| 2005/0100193 A1 | 5/2005 | Privalov |
| 2005/0264813 A1 | 12/2005 | Giakos |
| 2006/0091310 A1 | 5/2006 | Furry |
| 2006/0203238 A1 | 9/2006 | Gardner, Jr. et al. |
| 2006/0246592 A1 | 11/2006 | Hashmonay |
| 2006/0253570 A1 | 11/2006 | Biswas et al. |
| 2006/0263895 A1 | 11/2006 | Berkowitz et al. |
| 2007/0241280 A1 | 10/2007 | Dainobu et al. |
| 2008/0008625 A1 | 1/2008 | Thomas et al. |
| 2008/0063298 A1 | 3/2008 | Zhou et al. |
| 2008/0251724 A1 | 10/2008 | Baliga et al. |
| 2009/0039255 A1 | 2/2009 | Andrews et al. |
| 2009/0055102 A1 | 2/2009 | Laufer et al. |
| 2009/0095096 A1 | 4/2009 | Dean et al. |
| 2009/0140851 A1 | 6/2009 | Graves et al. |
| 2009/0200466 A1 | 8/2009 | Mammen et al. |
| 2009/0222207 A1 | 9/2009 | Bernhardt |
| 2009/0287624 A1 | 11/2009 | Rouat et al. |
| 2009/0290025 A1 | 11/2009 | Cetin et al. |
| 2009/0294666 A1 | 12/2009 | Hargel |
| 2010/0127173 A1 | 5/2010 | Schmidt |
| 2010/0145659 A1 | 6/2010 | Bausch et al. |
| 2010/0211333 A1 | 8/2010 | Pruet et al. |
| 2010/0230593 A1 | 9/2010 | Hill, Jr. |
| 2010/0231722 A1 | 9/2010 | Hill, Jr. et al. |
| 2010/0284570 A1 | 11/2010 | Grimberg |
| 2010/0301214 A1 | 12/2010 | Jonsson |
| 2010/0329512 A1 | 12/2010 | Nam et al. |
| 2011/0038507 A1 | 2/2011 | Hager |
| 2011/0215936 A1 | 9/2011 | Ansari et al. |
| 2011/0221599 A1 | 9/2011 | Hogasten |
| 2011/0282473 A1 | 11/2011 | Pavlovskaia et al. |
| 2012/0124029 A1 | 5/2012 | Kant |
| 2012/0153156 A1 | 6/2012 | Patel et al. |
| 2012/0262708 A1 | 10/2012 | Connolly |
| 2014/0002639 A1 | 1/2014 | Cheben et al. |
| 2014/0002667 A1 | 1/2014 | Cheben et al. |
| 2014/0354873 A1 * | 12/2014 | Parsons ......................... 348/342 |

FOREIGN PATENT DOCUMENTS

| | | |
|---|---|---|
| GB | 2 046 901 | 11/1980 |
| WO | WO93/11424 | 6/1993 |
| WO | WO 99/54700 | 10/1999 |
| WO | WO 2005/001409 | 1/2005 |
| WO | WO 2005/031321 | 4/2005 |
| WO | WO 2005/031323 | 4/2005 |
| WO | WO 2008/135654 | 11/2008 |
| WO | WO 2009/025560 | 2/2009 |
| WO | WO 2009/025561 | 2/2009 |
| WO | WO 2009/087614 | 7/2009 |
| WO | WO 2009/125413 | 10/2009 |
| WO | WO 2011/091091 | 7/2011 |
| WO | WO 2011/106796 | 9/2011 |
| WO | WO 2011/138766 | 11/2011 |
| WO | WO 2012/021753 | 2/2012 |
| WO | WO 2012/059339 | 5/2012 |
| WO | WO 2012/128764 | 9/2012 |
| WO | WO 2012/134796 | 10/2012 |
| WO | WO 2013/010272 | 1/2013 |
| WO | WO 2013/173541 | 11/2013 |

OTHER PUBLICATIONS

U.S. Appl. No. 62/015,921, filed Jun. 23, 2014, Morris et al.

U.S. Appl. No. 62/015,924, filed Jun. 23, 2014, Morris et al.

Zeng, et al., "The Third Generation LDAR (LDAR3) Lower Fugitive Emissions at a Lower Cost" (presented at the 2006 Environmental Conference of the National Petrochemical & Refiners Association, Sep. 18-19, 2006).

Hackwell, et al., "LWIR/MWIR Hyperspectral Sensor for Airborne and Ground-based Remote Sensing," Proceedings of the SPIE, Imaging Spectroscopy II, Aug. 7-8, 1996, pp. 102-107, vol. 2819, SPIE-The International Society for Optical Engineering, Bellingham, WA.

Orpen, "The Development and Optimisation of a Low Cost Optical Chemical Sensing Platform," Nov. 2010, Master Thesis in Mechanical Engineering, Dublin City University, Dublin 9, Ireland.

Zhou, et al., "Automatic Alignment of Infrared Video Frames for Equipment Leak Detection," Analytica Chimica Acta, retrieved from http://www.sciencedirect.com/science/journal/00032670/584/1, pp. 223-227, vol. 584, issue 1, Feb. 2007, Elsevier, Netherlands.

Histogram matching, Wikipedia, the free encyclopedia, XP0055206647, Retrieved from the Internet: https://en.wikipedia.org/w/index.php?title=Histogrammatching, 3 pgs. (Feb. 6, 2014).

Howe, J.D., "Two-color infrared full Stokes imaging polarimeter development," XP010350280, Aerospace Conference 1999, Aspen, CO, pp. 79-85 (Mar. 6, 1999).

(56) References Cited

OTHER PUBLICATIONS

"The Colour Image Processing Handbook," Section 8.2.1. Windowing, XP055182098, Springer-Science & Business Media, B.V., pp. 157-158 (1998).

Williams, T. et al., "Simultaneous correction of flat field and nonlinearity response of intensified charge-coupled devices," *Review of Scientific Instruments* 78, pp. 123702-1-123702-6, Dec. 13, 2007.

\* cited by examiner

METHODS FOR CALIBRATING A MULTIPLE DETECTOR SYSTEM

CROSS-REFERENCE TO RELATED APPLICATION

This application claims the benefit of U.S. Provisional Application No. 62/015,926, filed Jun. 23, 2014, entitled METHODS FOR CALIBRATING A MULTIPLE DETECTOR SYSTEM, the entirety of which is incorporated by reference herein.

FIELD

The present disclosure relates to systems and methods for identifying chemical species. More particularly, the present disclosure is related to systems and methods for calibrating a multiple detector system for detecting chemical species.

BACKGROUND

This section is intended to introduce various aspects of the art, which may be associated with one or more embodiments of the present disclosure. This discussion is believed to assist in providing a framework to facilitate a better understanding of particular aspects of the present disclosure. Accordingly, it should be understood that this section should be read in this light, and not necessarily as admissions of prior art.

Chemical usage is a fundamental aspect of current civilization. Facilities for the production, processing, transportation, and use of chemical species continue to be built in locations around the world. Thus, detection of chemical species is a continuing focus.

An example of chemical species detection is gaseous leak detection. As the efficiency of facilities becomes increasingly important, even minor losses of chemical species such as hydrocarbons can add to cost or create issues for regulatory agencies.

Hydrocarbons in facilities may be lost due to process limitations or process upsets leading to flaring or leaks. While some of these issues can be directly improved by design, leaks still provide a challenge, as they may occur on any number of different process equipment types. For example, leaks can originate from pipe flanges, valves, valve stems, sampling systems, and any number of other locations. As equipment is used and ages, leaks become increasing probable.

Conditions within a facility can increase the probability of leakage or exacerbate leaks when they do form. For example, facilities using high pressures or cryogenic temperatures can increase the probability of leaks. LNG plants are an example of such facility conditions. The number of LNG liquefaction plants around the world is growing rapidly and as these plants age, there is the increasing potential for hydrocarbon leaks to develop.

Early detection and repair of leaks can be useful in preventing any number of issues, such as increased costs and regulatory issues. Leaks may be detected by operators, for example, by visually observing the release, smelling the hydrocarbons, or hearing noise caused by the release. However, most hydrocarbon vapors are not visible to the naked eye. Further, there is often a high level of equipment congestion in plants, which may place a leak point behind another piece of equipment. In addition, hydrocarbons may have a minimal odor and, thus, may not be detected by smell. Detecting a small leak by sound is more improbable, as the very high level of ambient noise and safety equipment such as earplugs makes it unlikely that the leak will be heard.

Leak detection systems have been installed in many facilities. One such system may include combustible gas detectors that monitor the concentration or lower explosive limit (LEL) of hydrocarbon vapors at a particular location, providing a measurement of a hydrocarbon level at a point in an area. An array of point measurement systems may then be used to track a vapor release across the area. However, point detection systems may not detect small releases, such as from small leaks or new leaks, the amount of hydrocarbons released, and the like.

Another leak detection system that has been used utilizes a detection method that detects hydrocarbons in a line across a plant environment, for example, by directing a light source at one edge of an area towards a spectroscopic detector at another edge of the area. While such systems may be useful for monitoring compliance for regulatory issues, they do not necessarily identify a location of a release along the line. Further they may not detect small releases at all for the same reasons as the point detectors, e.g., the hydrocarbons may be too dilute to detect or may be blown away from the detection line by the wind.

Another leak detection system has been described that can detect releases by imaging areas using cameras which can directly show an image of a hydrocarbon plume. One such system is described in Hackwell, J. A., et al., "LWIR/MWIR Hyperspectral Sensor for Airborne and Ground-based Remote Sensing," Proceedings of the SPIE, Imaging Spectroscopy II, M. R. Descour, and J. M. Mooney, Eds., Vol. 2819, pp. 102-107 (1996). The system was named a spatially-enhanced broadband array spectrograph system (SEBASS). The SEBASS system was intended to explore the utility of hyperspectral infrared sensors for remotely identifying solids, liquids, and gases in a 2 to 14 micrometer spectral region often used to provide a chemical fingerprint. The SEBASS system allows the imaging and identification of chemical materials, such as hydrocarbon plumes, in an environment.

In a presentation entitled "The Third Generation LDAR (LDAR3) Lower Fugitive Emissions at a Lower Cost" (presented at the 2006 Environmental Conference of the National Petrochemical & Refiners Association, Sep. 18-19, 2006), Zeng, et al., discloses an autonomous system for leak detection that uses a camera to identify leaks in a particular area of a plant. Infrared (IR) video images from the camera are processed using software to minimize background and noise interference and the likely volatile organic compound (VOC) plumes are isolated using an algorithm. A plume index (PI) is calculated based on the number and intensity of pixels in the processed VOC plume image. If the PI is greater than an experimentally determined threshold value, an action can be triggered, such as an alarm or a video capture, for confirmation.

Another such system is described in WO2012/134796. The apparatus described therein includes multiple detectors configured to address complex interferences such as moving equipment, people, vehicles, or steam, which can lead to false detections with a single detector system.

While the existing systems attempt to minimize background and noise interference, there is still a desire to obtain improved images for more accurate detection of chemical species.

SUMMARY

This summary is meant to provide an introduction of the various embodiments further described herein and is not meant to limit the scope of claimed subject matter.

The present disclosure relates to a method of calibrating multiple electromagnetic (EM) radiation detectors within a detection system. The method includes generating a calibration electromagnetic radiation beam at a first temperature. At least a portion of the calibration electromagnetic radiation beam is detected with a first electromagnetic radiation detector. An average intensity value of a plurality of pixels of the first electromagnetic radiation detector detecting the calibration electromagnetic radiation beam is obtained. One or more pixels of the first electromagnetic radiation detector are adjusted to decrease the difference between the intensity of an individual pixel and the average intensity value of the first electromagnetic radiation detector. The method further includes detecting at least a portion of the calibration electromagnetic radiation beam with a second electromagnetic radiation detector. One or more pixels of the second electromagnetic radiation detector are adjusted to decrease the difference between the intensity of an individual pixel and the average intensity value of the first electromagnetic radiation detector.

In another aspect, the present disclosure relates to a method of detecting at least one chemical species. The method includes calibrating a detection system including multiple electromagnetic radiation detectors according to the embodiments disclosed herein; and using the calibrated detection system to determine the presence of the at least one chemical species.

Other aspects of the present disclosure will be apparent from the following description and the appended claims.

BRIEF DESCRIPTION OF THE DRAWINGS

The foregoing and other advantages of the present disclosure may become apparent upon reading the following detailed description and upon reference to the drawings, in which.

DETAILED DESCRIPTION

Figure 1:
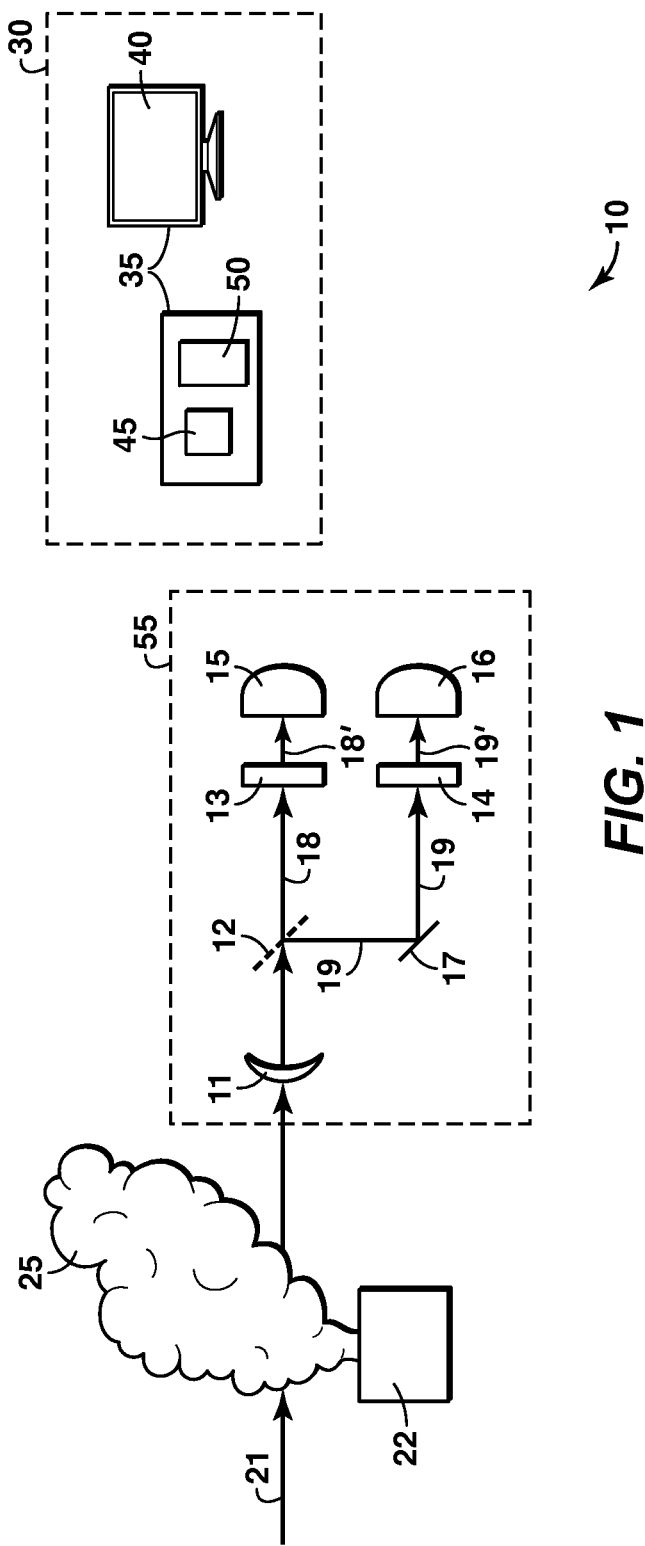
FIG. 1 illustrates a detection system in accordance with one or more embodiments of the present disclosure.

In the following detailed description section, the specific embodiments of the present disclosure are described in connection with one or more embodiments. However, to the extent that the following description is specific to a particular embodiment or a particular use of the present disclosure, this is intended to be for exemplary purposes only and simply provides a description of the one or more embodiments. Accordingly, the disclosure is not limited to the specific embodiments described below, but rather, it includes all alternatives, modifications, and equivalents falling within the true spirit and scope of the appended claims.

Various terms as used herein are defined below. To the extent a term used in a claim is not defined below, it should be given the broadest definition persons in the pertinent art have given that term as reflected in at least one printed publication or issued patent.

Certain terms are used throughout the following description and claims to refer to particular features or components. As one skilled in the art would appreciate, different persons may refer to the same feature or component by different names. This document does not intend to distinguish between components or features that differ in name only. The drawing figures are not necessarily to scale. Certain features and components herein may be shown exaggerated in scale or in schematic form and some details of conventional elements may not be shown in the interest of clarity and conciseness. When referring to the figures described herein, the same reference numerals may be referenced in multiple figures for the sake of simplicity. In the following description and in the claims, the terms "including" and "comprising" are used in an open-ended fashion, and thus, should be interpreted to mean "including, but not limited to."

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, quantities, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of 1 to 4.5 should be interpreted to include not only the explicitly recited limits of 1 to 4.5, but also to include individual numerals such as 2, 3, 4, and sub-ranges such as 1 to 3, 2 to 4, etc. The same principle applies to ranges reciting only one numerical value, such as "at most 4.5", which should be interpreted to include all of the above-recited values and ranges. Further, such an interpretation should apply regardless of the breadth of the range or the characteristic being described.

The term "electromagnetic radiation" or "EM radiation" shall mean electromagnetic waves or photons that carry energy from a source. EM radiation is often categorized into spectral ranges by its interaction with matter, for example radio waves, microwaves, infrared, visible light, ultraviolet light, x-rays, and gamma rays. As used herein, x-rays include wavelengths in the range of from 0.01 nanometers (nm) to 10 nm. Ultraviolet (UV) light, or the UV spectrum, includes light having wavelengths of 190 nm to 400 nm. Visible light or the visible spectrum includes light that is detectable by a human eye, for example from 400 nm to 700 nm. In the UV and visible spectral ranges, chemical species may absorb energy through electronic transitions in which an electron is promoted from a lower orbital to a higher orbital. IR light, or the IR spectrum, includes light at wavelengths longer than the visible spectrum but generally lower than the microwave region.

For example, the IR spectrum may include light having a wavelength between 0.7 micrometers (microns) and 14 microns (700 nm to 14000 nm) in length. At the longer wavelength end of this range, at 10 microns to 14 microns (the far IR), chemical species may absorb energy through rotational transitions. At an intermediate wavelength range of 2.5 microns to 10 microns (the mid-IR), chemical species may absorb energy through vibrational transitions. At the lower end of the wavelength range, at 0.7 microns to 2.5 microns (the near-IR), chemical species may absorb energy through vibrational transitions and through similar processes as visible and UV light, e.g., through electronic transitions. EM radiation detectors may form images from EM radiation in the visible spectrum, IR spectrum, or UV spectrum.

The term "camera" as used herein means a device that can obtain a two dimensional image or a sequence of two dimensional images or frames (such as video or series of still images) in a particular EM radiation spectral range.

The term "chemical species" is any compound that may be released into the environment as a gas, vapor, or liquid. Examples of chemical species that may be detected using the systems and methods described herein include both hydrocarbons and other chemical species. Chemical species that may be detected include but are not limited to hydrocarbon gas or vapors released in a cloud or plume into the air at an LNG plant or other facility or hydrocarbon liquids (e.g., oil) forming a slick on top of a body of water. Non-hydrocarbon species that may be detected include but are not limited to hydrogen fluoride gas released in a refinery, chlorine gas released in a water treatment facility, or any number of other liquids, gases, or vapors. A chemical species may also be deliberately added to a process stream to enhance the detection of a plume using the systems and methods described herein.

The term "facility" as used herein means any location including a tangible piece of physical equipment. For example, a tangible piece of physical equipment through which hydrocarbon fluids are produced from a reservoir, injected into a reservoir, processed, or transported. The term facility includes any equipment that may be present along the flow path between a reservoir and its delivery outlets. Facilities may include production wells, injection wells, well tubulars, wellhead equipment, gathering lines, manifolds, pumps, compressors, separators, surface flow lines, steam generation plants, processing plants, and delivery outlets. Examples of facilities include hydrocarbon production fields, polymerization plants, refineries, LNG plants, LNG tanker vessels, and regasification plants, among others.

The term "hydrocarbon" as used herein is an organic compound that primarily includes the elements hydrogen and carbon, although nitrogen, sulfur, oxygen, metals, or any number of other elements may be present in small amounts. As used herein, hydrocarbons generally refer to components found in natural gas, oil, or chemical processing facilities, such as refineries or chemical plants.

The term "natural gas" as used herein refers to a multi-component gas obtained from a crude oil well (associated gas) and/or from a subterranean gas-bearing formation (non-associated gas). The composition and pressure of natural gas can vary significantly. A typical natural gas stream contains methane ($CH_4$) as a major component, i.e., greater than 50 mol % of the natural gas stream is methane. The natural gas stream can also contain ethane ($C_2H_6$), higher molecular weight hydrocarbons (e.g., $C_3$-$C_{20}$ hydrocarbons), one or more acid gases (e.g., hydrogen sulfide), or any combinations thereof. The natural gas can also contain minor amounts of contaminants such as water, nitrogen, iron sulfide, wax, crude oil, or any combinations thereof.

The present disclosure provides methods for calibrating a detection system which includes multiple EM radiation detectors. In one or more embodiments, the detection system may be used to detect one or more chemical species released into the environment. It has been found that, when using detection methods as described in WO2012/134796, there can be variations between the two detectors. By matching the individual pixel intensity of the reference band EM radiation detector (e.g., the second EM radiation detector) to the average intensity of the chemical band EM radiation detector (e.g., the first EM radiation detector), an improved image quality can be obtained when using the detection system to determine the presence of a chemical species. This differential calibration method can decrease variability between the multiple detectors, increasing the ability to detect the presence of a chemical species that might otherwise be masked by the intensity response variability between detectors. For example, the differences in intensity between the chemical band EM radiation detector and the reference band EM radiation detector from independent calibration could be larger than the signal produced by the presence of a chemical species. This differential calibration method also improves image quality and helps reduce false positives from background and noise interference.

Any suitable detection system which includes multiple EM radiation detectors may be used. The multiple EM radiation detectors may include a first EM radiation detector configured to detect a chemical species (e.g., a chemical band EM radiation detector) and a second EM radiation detector configured to provide a reference background (e.g., a reference band EM radiation detector). FIG. 1 illustrates a detection system for detecting a chemical species according to one or more embodiments of the present disclosure. Although one or more embodiments may describe the use of the detection system to detect gaseous hydrocarbon releases such as leaks, the present description is not so limited. The systems and methods of the present disclosure may be used for detecting a chemical species in any application.

Referring to FIG. 1, detection system 10 includes a collection system 55. The collection system 55 including a lens 11 which receives IR rays 21 from a scene to be detected having passed through a gaseous vapor release of a chemical species 25 originating from container 22. The collection system 55 also includes a beam splitter 12 which receives the infrared rays 21 from the lens 11. The beam splitter 12 transmits a first EM radiation beam 18 to a first bandpass filter 13 and reflects a second EM radiation beam 19 to a second bandpass filter 14 reflected off mirror 17. Mirror 17 is optional; however, in the collection system depicted in FIG. 1, mirror 17 is provided so that first EM radiation detector 15 and second EM radiation detector 16 may be arranged parallel to one another (side-by-side). In embodiments without the use of a mirror, the second EM detector would be arranged ninety degrees (90°) from the first EM detector. Optionally, more than one mirror may be used to direct an EM radiation beam within the detection system. The filtered first EM radiation beam 18' is received by the chemical band EM radiation detector (the first EM radiation detector) 15 and the filtered second EM radiation beam 19' is received by the reference band EM radiation detector (the second EM radiation detector) 16. The detection system 10 may also include an analysis system 30. The analysis system 30 may include a computer system 35. The computer system 35 includes a display 40, a processor 45, and a non-transitory, computer-readable medium 50. The computer system 35 may be wired to one or more components of the collection system 55 or wirelessly connected to one or more components of the collection system 55. Although shown in FIG. 1 as separate analysis system 30 and computer system 35, in other embodiments, firmware may be installed within a processor; a non-transitory, computer-readable medium; or a combination thereof, within the collection system. In this certain embodiment, the firmware may include the code for directing the processor to perform the calibration or the analysis to detect a potential chemical species as well as other functions. Installing firmware within components of the collection system reduces the analysis required by a separate computer system.

The lens of the detection system may be any suitable lens. For example, the lens may be a fixed focal length lens or a multiple focal length lens (a zoom lens). The lens may be constructed of a material with high transmittance in a desired wavelength range. In one or more embodiments, the lens may be constructed of a silicon material or a germanium material for high transmittance in a mid-IR wavelength range.

The beam splitter may be any suitable beam splitter capable of receiving an EM radiation beam and splitting the EM radiation beam into a plurality of beams, for example at least two or more beams (first and second EM radiation beams or more), or at least three or more beams (first, second, and third EM radiation beams or more), or at least four or more EM radiation beams (first, second, third, and fourth EM radiation beams or more), or at least five or more EM radiation beams (first, second, third, fourth, and fifth EM radiation beams or more). In one or more embodiments, a beam splitter may be used to form two EM radiation beams which may be transmitted to an associated detector in the IR spectrum, and a separate lens may be used to transmit another EM radiation beam to an associated detector in the visible spectrum to infuse any detected chemical species into the visible image for easy human viewing.

In one or more embodiments, the beam splitter may be a broadband splitter or a prism.

In one or more embodiments, the beam splitter may be a broadband beam splitter. The broadband splitter may be constructed from a commercially available material which has approximately a 50% transmittance rate and a 50% reflectance rate. In one or more other embodiments, the broadband splitter may have a higher transmittance rate to one of the detectors. For example, the broadband splitter may have a transmittance rate of 60% or 70% or 80% or more to one of the detectors, while the remaining detectors receive 40% or 30% or 20% or less reflected from the broadband splitter. A broadband splitter transmits and reflects all wavelengths contained in the EM radiation beam received by the broadband beam splitter.

In one or more embodiments, the beam splitter may be a dichroic prism. A dichroic prism transmits the portion of the EM radiation beam with wavelengths below a cutoff wavelength value and reflects the portion of the EM radiation beam with wavelengths above the cutoff wavelength value. The dichroic prism may have a high transmittance rate, for example at least 80% or at least 90% or at least 95% or substantially 100% of the wavelengths below the cutoff wavelength value. The dichroic prism may have a high reflectance rate, for example at least 80% or at least 90% or at least 95% or substantially 100% of the wavelengths above the cutoff wavelength value.

In one or more embodiments, the cutoff value of the dichroic prism may be between a lower limit of the transmittance window of a chemical bandpass filter (e.g., the first bandpass filter) and the upper limit of the transmittance window of a reference bandpass filter (e.g., the second bandpass filter) when the transmittance window of the second bandpass filter is offset (at lower wavelengths) from the transmittance window of the first bandpass filter. In one or more other embodiments, the cutoff wavelength value of the dichroic prism may be between the upper limit of the transmittance window of a chemical bandpass filter (e.g., the first bandpass filter) and the lower limit of the transmittance window of a reference bandpass filter (e.g., the second bandpass filter) when the transmittance window of the second bandpass filter is offset (at greater wavelengths) from the transmittance window of the first bandpass window. For example, the cutoff wavelength value of the dichroic prism may be a value between the upper limit of the first transmittance window of the first bandpass filter and the lower limit of the second transmittance window of the second bandpass filter. As an exemplary embodiment, if the first transmittance window has a wavelength range between 3.25 microns and 3.45 microns (a 200 nm width) and the second transmittance window has a wavelength range between 3.7 microns and 4.1 microns (a 400 nm width), the cutoff wavelength value may be greater than 3.45 microns and less than 3.7 microns, such as 3.5 microns, 3.55 microns, 3.6 microns, or 3.65 microns.

In one or more embodiments, the cutoff wavelength value may be substantially halfway between the offset limits of the first and second transmittance windows. For example, the cutoff wavelength value may be substantially halfway between the upper limit of the first transmittance window and the lower limit of the second transmittance window or vice versa. In such an arrangement, the dichroic prism transmits the portion of the EM radiation beam having wavelengths less than the cutoff wavelength value and reflects the portion of the EM radiation beam having wavelengths greater than the cutoff wavelength value. In one or more other embodiments, the cutoff wavelength value of the dichroic prism may be greater than the upper limit of the transmittance window of the first bandpass filter or less than the lower limit of the first bandpass filter when the transmittance window for the second bandpass filter overlaps the transmittance window of the first bandpass filter. The cutoff wavelength value of the dichroic prism may be a value as further discussed herein.

In one or more embodiments, a chemical bandpass filter (e.g., a first bandpass filter) may be provided and may have a first transmittance window having a first width. The transmittance window of the first bandpass filter transmits EM radiation within a first EM radiation wavelength range and substantially rejects all other wavelengths outside the first transmittance window. The first EM radiation wavelength range of the first transmittance window may correspond to at least a portion of a wavelength range of absorption or emission by at least one chemical species to be detected. The transmittance window of the first bandpass filter (e.g., a first transmittance window) has a width (e.g., a first width) within an EM radiation wavelength range (e.g., a first EM radiation wavelength range). The transmittance window has a lower limit wavelength value and an upper limit wavelength value for the wavelength range. In one or more embodiments, the transmittance window for the first bandpass filter may have a width of at most 300 nm, at most 250 nm, at most 225 nm, at most 200 nm, at most 150 nm, or at most 100 nm or less. The width of the transmittance window for the first bandpass filter may be in the range of from 25 nm to 300 nm, from 50 nm to 250 nm, or from 75 nm to 200 nm.

The wavelength range of the transmittance window for the first bandpass filter may correspond to at least a portion of the wavelength range of absorption or emission by the at least one chemical species to be detected. In one or more embodiments, the transmittance window for the first bandpass filter is within the EM radiation spectrum, for example the IR spectrum such as the mid-IR spectrum. In one or more embodiments, the transmittance window for the first bandpass filter may have a lower limit of at least 2.5 microns, for example at least 3 microns, at least 3.25 microns, or at least 3.3 microns. In one or more embodiments, the transmittance window for the first bandpass filter may have an upper limit of at most 3.7 microns, for example at most 3.5 microns, at most 3.45 microns, or at most 3.4 microns, for example in the range of from 3 microns to 3.5 microns, from 3.25 microns to 3.45 microns, or from 3.3 microns to 3.4 microns. In one or more embodiments, the chemical species may be a hydrocarbon emitting or absorbing wavelengths within a range of from 3.2 microns to 3.5 microns.

The transmittance window of a chemical bandpass filter (e.g., the first bandpass filter) may transmit any suitable percentage of the first EM radiation beam within the wavelength range of the first transmittance window. In one or more embodiments, the transmittance window of the first bandpass filter may transmit at least 50% of the wavelengths of the first EM radiation beam received by the first bandpass filter within the wavelength range of the transmittance window. The transmittance window may transmit at least 75% or at least 80% or at least 90% or at least 95% or substantially 100% of the first EM radiation beam within the wavelength range of the transmittance window.

In one or more embodiments, a reference bandpass filter (e.g., a second bandpass filter) may be provided and may have a second transmittance window having a second width within an EM radiation wavelength range (e.g., a second EM radiation wavelength range). The second transmittance window passes or transmits EM radiation within a second EM radiation wavelength range and substantially rejects all other wavelengths outside the second transmittance window. The second transmittance window may be of any suitable width. In one or more embodiments, the second transmittance window may have an upper limit wavelength value that is greater than an upper limit wavelength value of the first transmittance window. In one or more embodiments, the width of the second transmittance window may be at least 50 nm, for example at least 100 nm, at least 200 nm, at least 275 nm, at least 300 nm, at least 350 nm, at least 400 nm, or at least 500 nm or more. For example, the width of the transmittance window may be in the range of from 50 nm to 2000 nm, from 275 nm to 1000 nm, or from 300 nm to 500 nm. In one or more embodiments, the transmittance window for the first bandpass filter may have a width less than, greater than or equal to the width of the second transmittance window for the second bandpass filter. For example, in certain embodiments the width of the second transmittance window may be less than the width of the first transmittance window when the second transmittance window has an upper limit wavelength value that is greater than the upper limit wavelength value of the first transmittance window. This decrease in width may be used to reduce the energy level of the filtered EM radiation beam having greater wavelengths (e.g., the filtered second EM radiation beam or the filtered reference band EM radiation beam), also helping to match the energy levels of the filtered first EM radiation beam and the filtered second EM radiation beam.

In one or more embodiments, the transmittance window of a reference bandpass filter (e.g., the second bandpass filter) may partially overlap at the upper limit or the lower limit of the first transmittance window or may completely overlap the transmittance window of a chemical bandpass filter (e.g., the first bandpass filter). For example, the lower limit of the second transmittance window (having an upper limit greater than the upper limit of the first transmittance window) may be less than the upper limit or less than the lower limit of the first transmittance window. In another example, the upper limit of the second transmittance window (having a lower limit less than the lower limit of the first transmittance window) may be greater than the lower limit or greater than the upper limit of the first transmittance window. In one or more embodiments, the second transmittance window may have a lower limit of at least 2 microns, at least 3 microns, or at least 3.3 microns or more and an upper limit of at most 5 microns, at most 4.5 microns, or at most 4 microns, for example in the range of from 3 microns to 5 microns, from 3 microns to 4 microns, or from 3.3 microns to 4 microns.

In one or more other embodiments, the transmittance window of a reference bandpass filter (e.g., the second bandpass filter) may be offset from the transmittance window of a chemical bandpass filter (e.g., the first bandpass filter). The amount of offset may vary; however, the offset may be sufficient to enable the EM radiation detectors to distinguish between the background of a scene and the chemical species to be detected within the scene. In other words, the transmittance window of the second EM radiation detector has an offset such that images from the second EM radiation detector include background EM radiation and are devoid of any emission or absorbance from chemical species to be detected. In one or more embodiments, the second transmittance window may be offset from the first transmittance window by at least 100 nm or at least 150 nm or at least 200 nm or more. For example, the lower limit wavelength value of the second transmittance window is greater than the upper limit wavelength value of the first transmittance window, e.g., the lower limit wavelength value of the second transmittance window may be at least 100 nm or at least 150 nm or at least 200 nm or more greater than the upper limit wavelength value of the first transmittance window. For example, the transmittance window for the first bandpass filter may be within the IR spectrum, for example the mid-IR spectrum as discussed herein, and the transmittance window for the second bandpass filter may have a lower limit of at least 3.5 microns or at least 3.7 microns and an upper limit of at most 4.5 microns or at most 4.25 microns or at most 4.1 microns or at most 4 microns, for example in the range of from 3.5 microns to 4.5 microns or from 3.7 microns to 4.1 microns.

The widths and wavelength ranges for the first transmittance window and the second transmittance window (e.g., partial overlap, complete overlap, or offset) of a chemical bandpass filter and a reference bandpass filter may vary by application, equipment, and chemical species to be detected, but may at least be sufficient to enable the detectors to distinguish between the background and the chemical species.

The transmittance window of a reference bandpass filter (e.g., the second bandpass filter) may transmit any suitable percentage of the EM radiation beam (e.g., the second EM radiation beam or the reference band EM radiation beam) within the wavelength range of the transmittance window (e.g., the second transmittance window). In one or more embodiments, the transmittance window of a reference bandpass filter (e.g., the second bandpass filter) may transmit a lesser percentage of the EM radiation beam (e.g., the second EM radiation beam) received by the bandpass filter than a chemical bandpass filter (e.g., the first bandpass filter) transmits of the EM radiation beam (e.g., the first EM radiation beam or the chemical band EM radiation beam) through its transmittance window, as described in U.S. Provisional Application Ser. No. 62/015,924, filed Jun. 23, 2014, and titled, "System for Detecting a Chemical Species and Use Thereof," which is incorporated herein by reference in its entirety. The second transmittance window may transmit less than 50% of the wavelengths within the wavelength range of the transmittance window, for example the second transmittance window may transmit at most 45%, at most 40%, at most 35%, at most 30%, at most 25%, or at most 20% of the second EM radiation beam within the wavelength range of the transmittance window. By decreasing the percentage of the second EM radiation beam transmitted to the detector by lowering the transmittance of the second bandpass filter, the energy level of the filtered second EM radiation beam more closely matches the energy level of the filtered first EM radiation beam, allowing substantially similar integration times and improving image quality between the chemical band and reference band EM radiation detectors.

The first EM radiation detector may receive at least a portion of the first filtered EM radiation beam from the first bandpass filter to detect the filtered first EM radiation beam. The second EM radiation detector may receive at least a portion of the filtered second EM radiation beam from the second bandpass filter to detect the filtered second EM radiation beam. In one or more other embodiments, the first EM radiation beam and the second EM radiation beam may be received by the associated EM radiation detector from the beam splitter without an intervening bandpass filter. In one or more embodiments, the EM radiation beam may be received by the associated EM radiation detector via one or more mirrors which may be used to direct the beam. The EM radiation detectors (e.g., the first and second EM radiation detectors) may be conventional EM radiation detectors configured to detect EM radiation. The detectors include one or more sensors configured to detect EM radiation in the appropriate wavelength range. The one or more sensors are configured to include a plurality of pixels to detect the intensity of the EM radiation received by the detector. For example, the sensors may include a focal plane array, a charge-coupled device (CCD), a complementary metal-oxide-semiconductor (CMOS), and any combinations thereof. In one or more embodiments, the one or more sensors of the EM radiation detectors may be included within a camera. In one or more embodiments, the camera may include the components described herein within the collection system. The collection system or camera may also include a readout integrated circuit (ROIC), video interface board, a field programmable gate array (FPGA), and any combinations thereof. The collection system or camera may also include a cooler such as a cryogenic cooler, for example an integrated dewar cooler assembly (IDCA), configured to cool the sensors in the EM radiation detectors. The EM radiation detectors are configured to communicate with the analysis system of the detection system. The communication components may provide wired or wireless communication.

In one or more embodiments, the EM radiation detectors may be configured to detect mid-IR EM radiation. The mid-IR EM radiation detector may include one or more focal plane arrays which may include a mercury-cadmium-telluride focal plane array, an indium-Antimonide focal plane array, an indium-gallium-arsenide focal plane array, a vanadium oxide focal plane array, and any combinations thereof. The mid-IR EM radiation detectors may include at least one cooler configured to cool the detector. Examples of gas-detecting IR cameras that are commercially available include GF320 and GF306 cameras manufactured by FLIR Systems, Inc., and EYE-C-GAS® camera manufactured by Opgal.

In one or more other embodiments, the multiple EM radiation detectors may include an EM radiation detector configured to detect visible or near-IR EM radiation. The visible or near-IR EM radiation detector may be a CCD, a CMOS, and any combinations thereof.

In one or more embodiments, the EM radiation beam forms an image on the associated EM radiation detector. The EM radiation detector may be configured to generate a single image, a plurality of still images, or a video of sequential images. Any number of EM radiation detectors may be used in a detection system, depending on the wavelength ranges to be detected. Thus, the multiple EM radiation detectors may be the same or different.

The detection system has an analysis system which may include a processor and non-transitory, computer-readable medium. The processor; the non-transitory, computer-readable medium; or combinations thereof may comprise code. The analysis system may also include a display. The analysis system may also include a graphical processing unit (GPU). The code is configured to direct the processor to: obtain an average intensity value of a plurality of pixels from a chemical band EM radiation detector (e.g., the first EM radiation detector) detecting the calibration EM radiation beam; adjust one or more pixels of an image from the first EM radiation detector to decrease the difference between the intensity of an individual pixel and the average intensity value of the first EM radiation detector; and adjust one or more pixels of a reference band EM radiation detector (e.g., the second EM radiation detector) detecting the calibration EM radiation beam to decrease the difference between the intensity of an individual pixel and the average intensity value of the first EM radiation detector. The code of the analysis system may be further configured to direct the processor to perform various other functions described herein.

Figure 2:
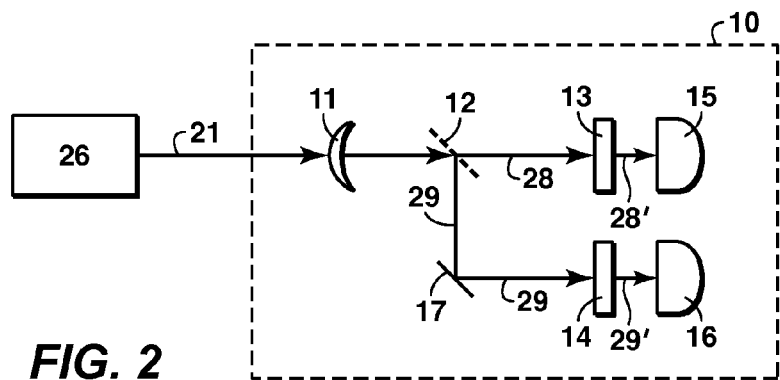
FIG. 2 illustrates a calibration system for calibrating the detection system in accordance with one or more embodiments of the present disclosure.

In the differential calibration method, a multiple detector system is calibrated by matching individual pixels of an image from a chemical band EM radiation detector (e.g., the first EM radiation detector) and individual pixels of an image from a reference band EM radiation detector (e.g., the second EM radiation detector) to the average intensity of the pixels of the chemical band EM radiation detector. Referring to FIG. 2, detection system 10 includes a lens 11 which receives IR rays 21 from a calibration EM radiation source 26. The detection system 10 also includes a beam splitter 12 which receives the infrared rays 21 from the lens 11. The beam splitter 12 transmits a first calibration EM radiation beam 28 to a first bandpass filter 13 and reflects a second calibration EM radiation beam 29 to a second bandpass filter 14 reflected off mirror 17. The filtered first calibration EM radiation beam 28' is received by the first EM radiation detector 15 and the filtered second calibration EM radiation beam 29' is received by the second EM radiation detector 16. Similar components of the detection system of FIG. 2 use the same reference numbers as in FIG. 1. The analysis system of the detection system is not shown.

Figure 3:
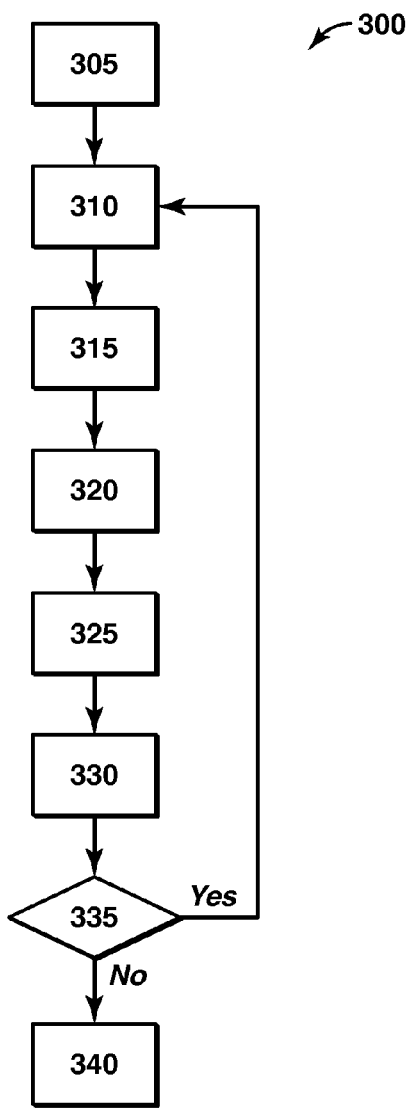
FIG. 3 illustrates a flow chart for a method of calibrating multiple electromagnetic radiation detectors within a system in accordance with one or more embodiments of the present disclosure.

Referring to FIG. 3, differential method 300 for calibrating a multiple detector system is illustrated according to one or more embodiments of the present disclosure. At block 305, the calibration method begins using a detection system as described herein. At block 310, a calibration EM radiation beam is generated using a calibration EM radiation source. The calibration EM radiation source may be any suitable source capable of providing a substantially uniform source of EM radiation for calibrating an EM radiation detector. The calibration EM radiation source is generated across the entire field of view of the EM radiation detectors. For example, the calibration EM radiation source may be a blackbody. The calibration EM radiation beam is generated by the source at a first temperature. The first temperature may be in the range of from minus 50° Celsius (C) to 250° C. or from 0° C. to 175° C. or from 5° C. to 150° C. or from 20° C. to 100° C.

At block 315, at least a portion of the calibration EM radiation beam is detected with the first EM radiation detector. The calibration EM radiation beam passes through the beam splitter to provide at least a first calibration EM radiation beam and a second calibration EM radiation beam. At least a portion of the first calibration EM radiation beam may pass through the first bandpass filter to generate a filtered first calibration EM radiation beam, at least a portion of which is detected by the first EM radiation detector. At least a portion of the second calibration EM radiation beam may pass through the second bandpass filter to generate a filtered second calibration EM radiation beam, at least a portion of which is detected by the second EM radiation detector.

At block 320, an average intensity (mean intensity) value of the calibration EM radiation beam detected by the first EM radiation detector is obtained. The average intensity value may be determined by calculating the average intensity of a plurality of pixels contained within a calibration image from the first EM radiation detector.

At block 325, one or more of the plurality of pixels of the first EM radiation detector are adjusted to decrease the difference between the intensity of an individual pixel and the average intensity value of the first EM radiation detector. The intensity of an individual pixel in the ROIC of the EM radiation detector may be adjusted by modifying the gain, offset, and combinations thereof, to yield a substantially uniform response across the pixels of the EM radiation detector. In one or more embodiments, after the calibration adjustment of the pixels of the first EM radiation detector, the difference between an individual pixel intensity and the average pixel intensity of the first EM radiation detector may be within at most 5% of the dynamic range of the sensor of the first EM radiation detector, for example within 1% or within 0.5% or within 0.1%.

At block 330, at least a portion of the calibration EM radiation beam is detected with the second EM radiation detector. At block 335, one or more of the plurality of pixels of the second EM radiation detector may be adjusted to decrease the difference between the intensity of an individual pixel and the average intensity value of the first EM radiation detector. Individual pixels may be adjusted in accordance with methods discussed herein. In one or more embodiments, the integration time of the chemical band EM radiation detector may be selected to maximize the sensitivity and adjust the dynamic range of the detector, and the integration time of the reference band EM radiation detector may be selected such that its integration time may be different than the chemical band EM radiation detector to assist in matching the energy level between the reference band EM radiation detector and the chemical band EM radiation detector within a single clock cycle, assisting in matching the resulting intensity levels between the chemical band EM radiation detector and the reference band EM radiation detector. In one or more embodiments, after the calibration adjustment of the pixels of the second EM radiation detector, the difference between an individual pixel intensity and the average pixel intensity of the first EM radiation detector may be within at most 5% of the dynamic range of the sensor of the second EM radiation detector, for example within 1% or within 0.5% or within 0.1%. In one or more embodiments, the intensity of a majority (more than 50%) of the plurality of pixels of the first EM radiation detector and a majority (more than 50%) of the plurality of pixels of the second EM radiation detector are substantially the same as the average intensity value for the first EM radiation detector after calibration adjustment.

If additional calibration is desired for additional temperatures, the method reverts back to block 310 and generates a calibration EM radiation beam at one or more additional temperatures. This may be repeated for any number of desired calibration temperatures. The additional calibration temperatures may be within the ranges discussed herein for the first calibration temperature but have different values. If no additional calibration temperatures are desired, the differential calibration method may end at block 340. Additionally, if more than two detectors are used in the detection system, the method may also include additional steps to calibrate the additional detectors, for example additional detectors similar to the first EM radiation detector may be calibrated by adjusting one or more pixels of the additional EM radiation detector to decrease the difference between the intensity of an individual pixel and the average intensity value of the first EM radiation detector, and additional detectors which are not similar to the first EM radiation detector, such as a visible EM radiation detector, may be calibrated using any appropriate calibration method for such detector.

In one or more embodiments, an image quality enhancement method may be applied to images from a chemical band EM radiation detector and a reference band EM radiation detector. Any suitable enhancement method may be used. In one or more embodiments, a differential image quality enhancement method may be applied to images from a chemical band EM radiation detector and a reference band EM radiation detector, as described in U.S. Provisional Application Ser. No. 62/015,921, filed Jun. 23, 2014, and titled, "Methods for Differential Image Quality Enhancement for a Multiple Detector System, Systems and Use Thereof," which is incorporated herein by reference in its entirety. The differential image quality enhancement analyzes the pixels from an image from the chemical band EM radiation detector to determine the gain and/or offset to be applied to images. The determined gain and/or offset is applied to the images from the chemical band EM radiation detector and also to the images of the reference band EM radiation detector. Adjusting the images from the reference band EM radiation detector using the gain and/or offset determined for the images from the chemical band EM radiation detector reduces the variability in intensity values between the detectors, increasing the ability to detect the presence of a chemical species that would otherwise be masked by the intensity response variability between detectors.

In such differential image quality enhancement, the analysis system may have code further configured to direct the processor to: identify an image from one or more images from a chemical band EM radiation detector (e.g., the first EM radiation detector), the image including a plurality of pixels, each pixel having an associated intensity value; identify an image from one or more images from a reference band EM radiation detector (e.g., the second EM radiation detector), the image including a plurality of pixels, each pixel having an associated intensity value; adjust one or more intensity values of the plurality of pixels of the image from the second EM radiation detector based on one or more intensity value parameters of the image from the first EM radiation detector; and adjust one or more intensity values of the plurality of pixels of the image from the first EM radiation detector based on one or more intensity value parameters of the image from the first EM radiation detector.

The differential image quality enhancement may be applied to the images automatically or through manual operator input. The adjustment values may be continually updated or periodically updated after a set number of images have been generated, for example no more than 50 successive images have been generated, or no more than 25 successive images have been generated, or no more than 15 successive images have been generated. With periodic updating, the determined adjustment values for the pixels may be applied to the pixels of subsequent images to enhance the image quality of those images until the adjustment values are updated.

The method for differential image quality enhancement may include obtaining an image from one or more images from a chemical band EM radiation detector (e.g., the first EM radiation detector). The chemical band image includes a plurality of pixels, each pixel having an associated intensity value. An image from one or more images from a reference band EM radiation detector (e.g., the second EM radiation detector) may be obtained. The reference band image includes a plurality of pixels, each pixel having an associated intensity value. One or more intensity values of the plurality of pixels of the image from the second EM radiation detector may be adjusted based on one or more intensity value parameters of the image from the first EM radiation detector. The adjusting of the one or more intensity values of the plurality of pixels may include adjusting the gain, offset, and combinations thereof based on one or more intensity value parameters of the image from the first EM radiation detector. The intensity value parameters may include a maximum intensity value for the plurality of pixels ($I_{max}$), a minimum intensity value for the plurality of pixels ($I_{min}$), and combinations thereof.

In one or more embodiments, the maximum intensity value, the minimum intensity value, and combinations thereof may be determined based on a subset of the plurality of pixels from an image from a chemical band EM radiation detector corresponding to an area of interest. A plurality of areas of interest may be identified in images relevant for applying the differential image quality enhancement. A maximum intensity value, a minimum intensity value, and combinations thereof may be determined for each of the areas of interest based on corresponding subsets of the plurality of pixels from an image from a chemical band EM radiation detector. Corresponding subsets of the plurality of pixels from an image from a reference band EM radiation detector may be adjusted based on the maximum intensity values, minimum intensity values, and combinations thereof for each of the areas of interest of the image from the chemical band EM radiation detector.

The detection system may be used in any facility that has hydrocarbons, or other detectable chemical species, present. Examples of such facilities include LNG plants, oil and gas wellhead operations, offshore platforms, transport pipelines, ships, trucks, refineries, and chemical plants, as described herein. As noted, the chemical plume may be a gaseous hydrocarbon or an oil slick on a surface of water, such as around an offshore platform, tanker, off-loading platform, and the like.

If a positive identification of a leak is made, the detection system may locate the leak and activate an alarm, alerting an operator to send a response team to the site of the leak. The response team may confirm the presence of the leak and effectuate repairs. In one or more embodiments, the hydrocarbon leak may be shown as a false color image for easier operator interpretation. Further, the system may have zoom capability to assist the operator when doing a leak investigation in a manual mode. In one or more embodiments, the EM radiation detectors may be able to be operated in both the automatic and manual modes. Thus, in the event of an alarm, an operator may be able to take control of the EM radiation detectors to do further investigation.

In one or more embodiments, the system may be configured to work over a broad temperature range, including warm and cold temperatures such as a hot, tropical, or desert environment or a cold, arctic environment. Further, the detection system may be adapted to function in the day or night and at a variety of temperatures, for example ranging from minus 50° C. to 100° C. The detection system may also be configured to operate under other environmental interferences, such as in fog, rain, or sandstorms. In one or more embodiments, the detection system may detect hydrocarbons, such as methane, ethane, propane, butane, pentane, hexane, heptane, octane, ethylene, propylene, isoprene, benzene, ethyl benzene, toluene, xylene, and methyl ethyl ketone, among others. The detection system may be additionally or alternatively configured to detect other chemical species which are capable of being imaged.

The present detection systems may utilize ambient EM radiation energy for the detection, but may also utilize artificial illumination sources for the EM radiation to detect a chemical species. In one or more embodiments, an EM radiation source, e.g., a light source, may be used to illuminate the environment. For example, an IR laser may be used to illuminate an area of interest for leak confirmation. The light source may be useful in conditions in which the contrast between a plume and the background may not be sufficient to distinguish the chemical species. The light source may be powered, activated, or moved using a light source control in communication with the present system.

The detection system is not limited to the detection of chemical plumes, but may also provide other functionality. For example, in one or more embodiments, the detection system may be used to detect an event other than the release of a chemical species such as to monitor specific equipment, such as furnaces, reactors, compressors, and the like, looking for such problems as hot spots, maldistribution, hot motors, and the like. Further, the detection system may provide fence-line monitoring for security purposes and monitoring of fugitive emissions into the environment from equipment.

In one or more embodiments, the detection system may include a master clock. The EM radiation detectors may be configured to receive a signal from the master clock to synchronize the frame rate and/or integration time of the EM radiation detectors. The synchronization may be accomplished through the clocking circuit in the ROIC of the EM radiation detectors. Such synchronization may improve the temporal alignment of the images. In one or more embodiments, one of the EM radiation detectors may be designated as the master and generates a clock signal to the other EM radiation detectors, which are designated as a slave to the master EM radiation detector and receive the clock signal. The resulting frame rate of each EM radiation detector is then synchronized to the shared clock signal.

In one or more embodiments, images from the chemical band EM radiation detector and the reference band EM radiation detector may be spatially aligned. Images may be spatially aligned using any suitable method. In one or more embodiments, spatial alignment may be accomplished by keeping the EM radiation detectors stationary. In one or more other embodiments, the images may be registered such that a software program may provide spatial alignment using a software registration method which uses features in the image for alignment. In one or more embodiments, the EM radiation detectors may be configured to be substantially spatially aligned. In one or more embodiments, the EM radiation detectors may be both substantially temporally and spatially aligned. The images may be registered such that the images may be substantially matched in spatial alignment pixel by pixel, temporal alignment, or the combination thereof.

In one or more embodiments, the integration times of the EM radiation detectors may be substantially the same or different. In one or more embodiments, the integration time of a chemical band EM radiation detector (e.g., the first EM radiation detector) may be substantially the same as the integration time of a reference band EM radiation detector (e.g., the second EM radiation detector) and the transmittance of a reference bandpass filter (e.g., the second bandpass filter) may be less than a chemical bandpass filter (e.g., the first bandpass filter) as described herein. By decreasing the transmittance of a reference bandpass filter, the energy level of the resulting filtered EM radiation beam can more closely match the energy level of a filtered chemical band EM radiation beam, assisting in matching the resulting intensity levels between the chemical band EM radiation detector and the reference band EM radiation detector.

In one or more other embodiments, the integration time of a reference band EM radiation detector (e.g., the second EM radiation detector) may be different than the chemical band EM radiation detector (e.g., the first EM radiation detector) to assist in matching the energy level between the reference band EM radiation detector and the chemical band EM radiation detector within a single clock cycle, assisting in matching the resulting intensity levels between the chemical band EM radiation detector and the reference band EM radiation detector. For example, the integration time of a reference band EM radiation detector (e.g., the second EM radiation detector) may be less than the integration time of a chemical band EM radiation detector (e.g., the first EM radiation detector). In one or more embodiments, the integration time of the second EM radiation detector may be at most 95% of the integration time of the first EM radiation detector, for example at most 75%, at most 50%, at most 40%, or at most 33% of the integration time of the first EM radiation detector. When the energy level of the reference band EM radiation beam is greater than the chemical band EM radiation beam, decreasing the integration time of a reference band EM radiation detector (e.g., the second EM radiation detector) can more closely match the energy levels of the EM radiation beams, assisting in matching the resulting intensity levels between the chemical band EM radiation detector and the reference band EM radiation detector. Conversely, when the energy level of the chemical band EM radiation beam is greater than the reference band EM radiation beam, decreasing the integration time of a chemical band EM radiation detector (e.g., the first EM radiation detector) can more closely match the energy levels of the EM radiation beams. However, significant differences in integration times can result in image blurring due to the time differences, reducing image quality.

In one or more embodiments, the method of detecting a chemical species may include identifying at least one image of a scene to be detected by a chemical band EM radiation detector (e.g., the first EM radiation detector) and at least one image of a scene to be detected by a reference band EM radiation detector (e.g., the second EM radiation detector); comparing the image from the first EM radiation detector with the image from the second EM radiation detector; and determining if a difference between the images represents the detection of a chemical species.

In one or more embodiments, determining the presence of at least one chemical species may include generating a resultant image. The resultant image may be based, at least in part, on the data generated by the first and second EM radiation detectors, for example a single image, a series of still images, or video images generated by the detectors. The presence or absence of a chemical species may be determined based, at least in part, on any differences existing in the resultant image. Subsequent resultant images may be generated to provide greater accuracy in the identification of a potential release, decreasing false positives resulting from background and noise interference.

In one or more embodiments, a preliminary threshold criteria may be applied to the pixels from images from a chemical band EM radiation detector and images from a reference band EM radiation detector to remove pixels satisfying the preliminary threshold criteria from further consideration. The preliminary threshold criteria may include at least a first preliminary threshold value and a second preliminary threshold value. Pixels having intensity values greater than the first preliminary threshold value may be removed from further consideration. Pixels having intensity values less than the second preliminary threshold value may be removed from further consideration.

A resultant image (e.g., a first resultant image) may be formed by comparing an image (e.g., a first image) from a chemical band EM radiation detector (e.g., the first EM radiation detector) with an image (e.g., a second image) from a reference band EM radiation detector (e.g., the second EM radiation detector). In one or more embodiments, a plurality of resultant images (e.g., a first resultant image, a second resultant image, a third resultant image, etc.) may be analyzed. The plurality of resultant images may be formed from a plurality of images from the chemical band EM radiation detector (e.g., a first image, a third image, a fifth image, etc.) and a plurality of images from the reference band EM radiation detector (e.g., a second image, a fourth image, a sixth image, etc.). Determining the presence or absence of a chemical species may be based, at least in part, on one or more resultant images. A resultant image may be formed in any suitable manner, for example by determining the differences between intensity values of corresponding pixels of an image from a chemical band EM radiation detector and an image from a reference band EM radiation detector. One or more regions of interest may be identified based, at least in part, on non-zero intensity values for the resultant pixels. Differences observed in a resultant image may be considered a "positive" reading, i.e., an indication of the potential presence of a chemical species.

In one or more embodiments, the difference in intensity values of a resultant image may be formed by subtracting pixel intensities of an image from a reference band EM radiation detector (e.g., the second EM radiation detector) from pixel intensities of an image from a chemical band EM radiation detector (e.g., the first EM radiation detector). Subtracting pixel intensities of images yields a differential resultant image capturing a potential chemical species detected. One or more substantially spatially and/or temporally aligned pixels from the images (e.g., the first image and the second image) may be subtracted and the resulting intensity value used for the associated pixel in the resultant image (e.g., a first resultant image). The difference in intensity values in a resultant image may be represented by both the sign and the magnitude or may be absolute values.

In one or more other embodiments, the difference in intensity values of a resultant image may be determined by calculating the ratio between pixel intensities of an image from a reference band EM radiation detector (e.g., the second EM radiation detector) and pixel intensities of an image from a chemical band EM radiation detector (e.g., the first EM radiation detector). Calculating the ratio of pixel intensities of images yields a differential resultant image capturing any potential chemical species detected. The pixels of the images may be substantially spatially and/or temporally aligned. In one or more embodiments, the ratio is calculated between a plurality of pixels of an image from a chemical band EM radiation detector (e.g., the first EM radiation detector) and a plurality of pixels of an image from a reference band EM radiation detector (e.g., the second EM radiation detector). The ratio values are used to represent the intensity value for resultant pixels of the corresponding resultant image.

In one or more embodiments, a resultant threshold criteria may be applied to the resultant pixel intensity values. At least a portion of the resultant pixel values satisfying the resultant threshold criteria may be grouped into one or more regions of interest. The resultant threshold criteria includes at least one threshold value. In one or more embodiments, resultant pixels having an intensity value greater than a threshold value, and optionally additionally having the same sign, may be considered for inclusion in a region of interest. Taking into consideration the sign of the intensity of the resultant pixels may be used to remove resultant pixels from consideration due to low contrast, high noise such as those produced by vegetative backgrounds or highly reflective surfaces.

In one or more embodiments, the detection of a chemical species may be further enhanced using correlation coefficients as described in U.S. Provisional Application Ser. No. 62/015,920, filed Jun. 23, 2014, and titled, "Method and Systems for Detecting a Chemical Species", which is incorporated herein by reference in its entirety. For each of the one or more regions of interest identified in a resultant image, correlation coefficients may be determined. Each of the one or more regions of interest includes a subset of the plurality of pixels of the image. For example, one of the one or more regions may include a first subset of pixels from a plurality of pixels of an image from a chemical band EM radiation detector and a first subset of pixels from a plurality of pixels of an image from a reference band EM radiation detector and a first subset of pixels from a resultant image generated from the images. Another of the one or more regions of interest may include a second subset of pixels from the plurality of pixels of the image from the chemical band EM radiation detector and a second subset of pixels from the plurality of pixels of the image from the reference band EM radiation detector and a second subset of pixels from the resultant image generated from the same images. Additional regions of interest may include third subsets of pixels, fourth subsets of pixels, etc. Correlation coefficients (e.g., a first correlation coefficient, a second correlation coefficient, and a third correlation coefficient) may be calculated for each of the one or more regions of interest using the corresponding subset of pixels of the images. In one or more embodiments, the one or more regions of interest may be substantially the same as or different from the one or more areas of interest identified for any differential image quality enhancement methods described herein.

A correlation coefficient may be calculated using any suitable method. In one or more embodiments, the correlation coefficients may be calculated using a root mean square (RMS) correlation method to determine the correlation between corresponding pixel intensities within a region of interest to be correlated (e.g., the first image, the second image and the first resultant image; the third image, the fourth image, and the second resultant image; the fifth image, the sixth image, and the third resultant image; etc.). A greater correlation between images of the chemical band EM radiation detector and the corresponding resultant image (e.g., first correlation coefficients) versus the correlation between images of the reference band EM radiation detector and the corresponding resultant image (e.g., second correlation coefficients) and optionally the correlation between images of the chemical band EM radiation detector and images of the reference band EM radiation detector (e.g., third correlation coefficients) may indicate the presence of a chemical species for a region of interest. In one or more embodiments, a plurality of regions of interest may be identified for analysis in a resultant image. Correlation coefficients for each of the plurality of regions of interest may be calculated using the intensity values of the corresponding pixels from an image from the chemical band EM radiation detector, an image from the reference band EM radiation detector, and the resultant image, similar to the calculations for the first, second, and third correlation coefficients of the first region of interest. Different subsets of the plurality of pixels corresponding to the regions of interest may be used to determine the correlation between images for the particular region of interest.

In one or more embodiments, the code of the analysis system may additionally be configured to direct the processor to: identify at least one image from the first electromagnetic radiation detector and at least one image from the second electromagnetic radiation detector; compare the at least one image from the first EM radiation detector with the at least one image from the second EM radiation detector; and determine if a difference between the images represents the detection of a chemical species. The code may additionally be configured to direct the processor to: generate at least one resultant image, the resultant image including a plurality of resultant pixels, each pixel having an associated intensity value; determine one or more regions of interest based, at least in part, on the at least one resultant image; generate a plurality of correlation coefficients for at least one of the one or more regions of interest; and determine the presence of at least one chemical species based, at least in part, on the plurality of correlation coefficients. The detection method may additionally include generating a resultant image (e.g., at least a first resultant image); determining one or more regions of interest based, at least in part, on the resultant image; and determining correlation between an image (e.g., a first image) from the chemical band EM radiation detector (e.g., the first EM radiation detector), an image (e.g., the second image) from the reference band EM radiation detector (e.g., the second EM radiation detector), and the resultant image (e.g., the first resultant image) for at least one of the one or more regions of interest using a correlation coefficient algorithm to: calculate a first correlation coefficient, a second correlation coefficient, and optionally a third correlation coefficient.

The first correlation coefficient may be calculated using the intensity values of a first subset of pixels from the first plurality of pixels and a corresponding subset of resultant pixels from the plurality of resultant pixels within one of the one or more regions of interest. The second correlation coefficient may be calculated using the intensity values of a first subset of pixels from the second plurality of pixels and the corresponding subset of resultant pixels from the plurality of resultant pixels within the corresponding region of interest. The third correlation coefficient may be calculated using the intensity values of the first subset of pixels from the first plurality of pixels and the first subset of pixels within the corresponding region of interest. Additional correlation coefficients may be calculated for each of the additional regions of interest of the first image, the second image, and the first resultant image (e.g., a first correlation coefficient for an additional region of interest based on a second subset of pixels from the first image and the corresponding resultant pixels from the first resultant image; a second correlation coefficient for the additional region of interest based on a second subset of pixels from the second image and the corresponding resultant pixels from the first resultant image; and a third correlation coefficient for the additional region of interest based on the second subset of pixels from the first image and the second subset of pixels from the second image; etc.).

In one or more embodiments, the detection method includes providing a beam of EM radiation which is split into a first EM radiation beam and a second EM radiation beam. At least a portion of the first EM radiation beam is passed through a first bandpass filter forming a filtered first EM radiation beam and at least a portion of the second EM radiation beam is passed through a second bandpass filter forming a filtered second EM radiation beam. At least a portion of the filtered first EM radiation beam is received by the first EM radiation detector and at least a portion of the filtered second EM radiation beam is received by the second EM radiation detector. A first resultant image may be generated. The first resultant image is based, at least in part, on the data generated by the first and second EM radiation detectors, for example a single image, a series of still images, or video images generated by the detectors. The presence or absence of a chemical species is determined based, at least in part, on differences in the images from the first EM radiation detector and the second EM radiation detector. Subsequent images may be generated to provide greater accuracy in the identification of a potential release and decreasing false positives resulting from background and noise interference.

A number of variations to the detection analysis techniques disclosed herein may be used to improve the reliability, ease of use, or ease of implementation of the detection system. In one or more embodiments, leak modeling results, leak detection criteria, camera and lens characteristics, and algorithm requirements may be combined to form deployment reference charts for setting up an autonomous detection system.

In one or more embodiments, additional detection analysis methods may be utilized to enhance the determination of the presence or absence of a chemical species and/or to increase the accuracy of the analysis. The additional detection analysis methods may be applied to chemical band images, reference band images, resultant images, and any combinations thereof. Additional analysis methods are described herein and further described in U.S. Patent Publication No. 2014/0002639 and U.S. Patent Publication No. 2014/0002667, which are incorporated herein by reference in their entirety.

Image analysis methods may use an algorithm to further analyze the images to distinguish chemical species (e.g., a gaseous plume of a chemical species) from other features in an image to improve accuracy and decrease the probability of false alarms. The algorithm may further distinguish the chemical species, such as hydrocarbon gas or vapor, from other ambient factors, such as water flows, steam plumes, furnace off gases, vehicles, persons, wildlife, and the like. In addition to using resultant images to determine the presence of a chemical species, enhanced identification techniques may be used. Such enhanced identification techniques may include analyzing for features such as deterministic features, probabilistic features, auxiliary features, and any combinations thereof. The image(s) may be in color or in grayscale, in which the difference in contrast may be used to identify features.

An additional detection analysis method may include analyzing for a deterministic feature. Deterministic features may include both spatial and kinematic features, among others. For example, the additional analysis method may determine geometric features, including the shape of a chemical plume and/or the size of a chemical plume, among others. The analysis may also determine shape constraints such as aspect ratio, dispersiveness (e.g., the thickness of the plume as a function of distance), convexity, and histogram of orientation gradient (HOG) of contour, among others. These features serve as constraints and provide screening of the potential regions which may represent a chemical species.

Kinematic or motion features may include determining that a plume is constantly moving but that the motion is restricted to a constrained area, as may be expected by a plume originating from a leak. Kinematic features may include size constraints of a plume, such as a minimal and maximal size through a sequence of images. The kinematic features may be used to filter out most rigid body interferences.

Probabilistic features may include a spatial pattern of the chemical plume, a temporal pattern of the chemical plume, or any number of other features. The additional analysis method may include joint spatial and temporal analyses such as a fast dynamic texture algorithm. In the probabilistic analysis, a statistical model described by two types of equations, e.g., evolution equations and observation equations, which respectively model the way the intrinsic state evolves with time and the way the intrinsic state projects to image pixels, may be fitted to the segmented pixel data. Parameters may be estimated by matrices. Other probabilistic analysis techniques may also be used, such as principal component analysis (PCA). In PCA, a determination of the variables causing changes to a plume is made, such as a statistical comparison of wind speed and direction with changes seen in plumes.

Auxiliary features may include comparing images visible to the human eye to the plume identified using the non-visible images, such as images in the IR spectrum. For example, the visible images may be used to differentiate organic vapor plumes and water steam. Generally, organic plumes may be dark in the non-visible images and not very visible in the visible images. In contrast, a steam plume may be bright in the non-visible images, due to emitted heat, and visible in the visible images. In addition to improving the detection, the visible images may be used to locate the leak in the plant environment, for example, by comparing a registered image from a detector in the infrared spectrum with an overlapping image from a detector in the visible spectrum.

The detection and confirmation of plumes may be enhanced by meteorological measurements collected by a meteorological monitor. The meteorological monitor may collect data on environmental conditions such as wind speed, temperature, precipitation, atmospheric haze, and the like. This data may then be used in one or more embodiments to confirm that a detected plume is consistent with the collected data. For example, the calculated motion of the plume may be compared with the wind direction, such as in a PCA algorithm. If the motion of the plume is inconsistent with the wind direction, the plume identification may be incorrect.

The code of the analysis system may be further configured to direct the processor to provide additional detection analysis, for example configured to direct the processor to analyze one or more images (e.g., chemical band images, reference band images, resultant images, and any combinations thereof) for deterministic features, probabilistic features, auxiliary features, and any combinations thereof.

In one or more embodiments, the detection reliability and/or accuracy may also be improved by utilizing chemical markers in various hydrocarbon streams. The chemical markers may be substances added to increase an absorbance or emission at a particular wavelength. Such markers may make the use of other detection techniques more effective. For example, fluorescent chemicals may be added to a hydrocarbon stream in very small amounts, such as a few parts-per-million, as these compounds often have a high quantum yield, which is the number of photons emitted divided by the number of photons absorbed. As the wavelength of light emitted may not overlap with natural sources, the identification of a plume from the fluorescence may be straightforward.

In one or more embodiments, EM radiation detectors having different bit depths and dynamic intensity ranges may be used. In such situations, the values applied to pixels of one of the EM radiation detectors may be adjusted proportionally.

It should be understood that the preceding is merely a detailed description of specific embodiments of the invention and that numerous changes, modifications, and alternatives to the disclosed embodiments can be made in accordance with the disclosure here without departing from the scope of the invention. Although the detection system may be described herein with reference to a first, chemical band EM radiation detector and a second, reference band EM radiation detector, one skilled in the art in light of the present disclosure will appreciate that any number of additional detectors may be used with the detection system described herein. The preceding description, therefore, is not meant to limit the scope of the invention. Rather, the scope of the invention is to be determined only by the appended claims and their equivalents. It is also contemplated that structures and features embodied in the present examples can be altered, rearranged, substituted, deleted, duplicated, combined, or added to each other. The articles "the", "a" and "an" are not necessarily limited to mean only one, but rather are inclusive and open-ended so as to include, optionally, multiple such elements.

What is claimed is:

1. A method of calibrating multiple electromagnetic radiation detectors within a detection system comprising:
   generating a calibration electromagnetic radiation beam at a first temperature;
   detecting at least a portion of the calibration electromagnetic radiation beam with a first electromagnetic radiation detector;
   obtaining an average intensity value of a plurality of pixels of the first electromagnetic radiation detector detecting the calibration electromagnetic radiation beam;
   adjusting one or more pixels of the first electromagnetic radiation detector to decrease the difference between the intensity of an individual pixel and the average intensity value of the first electromagnetic radiation detector;
   detecting at least a portion of the calibration electromagnetic radiation beam with a second electromagnetic radiation detector; and
   adjusting one or more pixels of the second electromagnetic radiation detector to decrease the difference between the intensity of an individual pixel and the average intensity value of the first electromagnetic radiation detector.

2. The method of claim 1 further comprising:
   passing the calibration electromagnetic radiation beam through a beam splitter to provide a first calibration electromagnetic radiation beam and a second calibration electromagnetic radiation beam;
   passing at least a portion of the first calibration electromagnetic radiation beam through a first bandpass filter; and
   passing at least a portion of the second calibration electromagnetic radiation beam through a second bandpass filter.

3. The method of claim 1, wherein the calibration electromagnetic radiation beam is obtained using a black body electromagnetic radiation source.

4. The method of claim 1, wherein the first temperature is between about minus 50° C. to about 200° C.

5. The method of claim 1 further comprising:
   generating an additional calibration electromagnetic radiation beam at a second temperature;
   detecting at least a portion of the additional calibration electromagnetic radiation beam with a first electromagnetic radiation detector;
   obtaining an average intensity value of the plurality of pixels of the first electromagnetic radiation detector detecting the additional calibration electromagnetic radiation beam;
   adjusting one or more pixels of the first electromagnetic radiation detector to decrease the difference between the intensity of an individual pixel and the average intensity value of the first electromagnetic radiation detector;
   detecting at least a portion of the additional calibration electromagnetic radiation beam with a second electromagnetic radiation detector; and
   adjusting one or more pixels of the second electromagnetic radiation detector to decrease the difference between the intensity of an individual pixel and the average intensity value of the first electromagnetic radiation detector.

6. The method of claim 5, wherein the second temperature is between about 20° C. to about 100° C. and is different from the first temperature.

7. The method of claim 1, wherein the calibration electromagnetic radiation is mid-wave infrared radiation.

8. The method of claim 1, wherein the first electromagnetic radiation detector comprises a first focal plane array and the second electromagnetic radiation detector comprises a second focal plane array.

9. The method of claim 1, wherein the intensity of a majority of the plurality of pixels of the first electromagnetic radiation detector and a majority of the plurality of pixels of the second electromagnetic radiation detector are substantially the same as the average intensity value for the first electromagnetic radiation detector.

10. The method of claim 1, wherein the difference between the plurality of pixels of the first electromagnetic radiation detector and the average intensity value of the first electromagnetic radiation detector is within 5% of the dynamic range of the first electromagnetic radiation detector.

11. The method of claim 1, wherein the difference between the plurality of pixels of the second electromagnetic radiation detector and the average intensity value of the first electromagnetic radiation detector is within 5% of the dynamic range of the second electromagnetic radiation detector.

12. The method of claim 2, wherein the first bandpass filter has a first transmittance window having a first width between a lower limit wavelength value and an upper limit wavelength value and the second bandpass filter has a second transmittance window having a second width between a lower limit wavelength value and an upper limit wavelength value such that the lower limit wavelength value and the upper limit wavelength value of the second transmittance window is outside of the lower limit wavelength value and the upper limit wavelength value for the first transmittance window.

13. The method of claim 1, wherein the difference between the intensity of an individual pixel and the average intensity value of the first electromagnetic radiation detector is decreased by adjusting the gain of the individual pixel.

14. The method of claim 1, wherein the difference between the intensity of an individual pixel and the average intensity value of the first electromagnetic radiation detector is decreased by adjusting the offset of the individual pixel.

15. A method of detecting at least one chemical species comprising:

calibrating a detection system including multiple electromagnetic radiation detectors according to claim 1; and using the calibrated detection system to determine the presence of at least one chemical species.

16. The method of claim 15, wherein the at least one chemical species originates from a release into the environment.

* * * * *